United States Patent [19]

Pinchuk

[11] Patent Number: 5,053,048

[45] Date of Patent: Oct. 1, 1991

[54] THROMBORESISTANT COATING

[75] Inventor: Leonard Pinchuk, Miami, Fla.

[73] Assignee: Cordis Corporation, Miami, Fla.

[21] Appl. No.: 610,465

[22] Filed: Nov. 8, 1990

Related U.S. Application Data

[63] Continuation of Ser. No. 247,944, Sep. 22, 1988, abandoned.

[51] Int. Cl.⁵ ............................................. A61F 2/06
[52] U.S. Cl. ........................................ 623/1; 623/66; 604/266; 128/DIG. 21; 523/112; 427/2
[58] Field of Search .............. 623/1, 8, 15, 66; 523/112; 427/2; 128/DIG. 21; 606/231; 604/266

[56] References Cited

U.S. PATENT DOCUMENTS

| | | | |
|---|---|---|---|
| 3,434,869 | 3/1969 | Davidson | 604/266 |
| 3,639,141 | 2/1972 | Dyck | |
| 3,708,324 | 1/1973 | Stebleton | 623/66 X |
| 3,844,989 | 10/1974 | Harumiya et al. | |
| 3,846,353 | 11/1974 | Grotta | 523/112 |
| 4,521,564 | 6/1985 | Solomon et al. | |
| 4,600,613 | 7/1986 | Yoshida | 604/408 |
| 4,820,302 | 4/1989 | Woodroof | 623/8 |
| 4,851,009 | 7/1989 | Pinchuk | 623/1 |
| 4,906,465 | 3/1990 | Chaikof et al. | 623/1 |

OTHER PUBLICATIONS

Larm et al., "A New Non-Thrombogenic Surface Prepared by Selective Covalent Binding of Heparin Via a Modified Reducing Terminal Residue," *Biomat., Med. Dev., Art. Org.*, 11 (2&3), 161–173, 1983.

*Primary Examiner*—David J. Isabella
*Assistant Examiner*—Paul Prebilic
*Attorney, Agent, or Firm*—Lockwood, Alex, Fitzgibbon & Cummings

[57] ABSTRACT

A thromboresistant coating, method for forming same on a medical device, and the medical device thus prepared are provided. The thromboresistant coating is a highly cross-linked three-dimensional matrix copolymerized from an aminosilane component and a silane other than the aminosilane that is cured and dried into a thick matrix having amino groups interspersed therethroughout. The amino groups facilitate attachment of an antithrombogenic agent to the matrix and thus to the medical device. In addition, an antithrombogenic material is secured to the aminosilane copolymeric matrix.

9 Claims, No Drawings

THROMBORESISTANT COATING

This application is a continuation of application Ser. No. 247,944, filed Sept. 22, 1988, now abandoned.

BACKGROUND AND DESCRIPTION OF THE INVENTION

The present invention generally relates to thromboresistant coatings for medical devices having a blood-contacting surface, as well as to methods for forming such coatings and to the medical devices thus formed More particularly, the invention relates to a polymeric matrix formed from an aminosilane homopolymer or copolymer, this matrix being formed on the surface of a medical device which is intended for contacting blood and the like when in use. An antithrombogenic agent is secured to the matrix to provide the thromboresistant coating.

A well-recognized problem in the medical community is the development of a thrombus or blood clot or obstruction that forms when any of a number of devices are used either within the body or within systems wherein blood or other body fluids are contacted or circulated. Exemplary of medical devices for which this problem is a concern are catheters, vascular grafts, cardiac pacer leads, heart diaphragms, sutures, needles, angioplasty devices, glass beakers, dialysis membranes, filters, sensors, monitors and the like. These types of medical devices will typically exhibit a variety of surfaces that contact blood or other body fluids. Representative materials in this regard include polytetrafluoroethylenes, polyamides, polyesters, polyurethanes, polysiloxanes, polyolefins, metals and the like.

An example of an approach that was directed toward this problem is found in United States Letters U.S. Pat. No. 3,639,141 to Dyck, which is incorporated by reference hereinto. That patent states that plastics are rendered nonthrombogenic by heparinizing them following treatment with an aminosilane in an inert solvent which preferably swells the plastic. A preliminary treatment with sodium is taught. The Dyck patent teaches immersing the plastic component in silane solution, washed in pure solvent and immersed in a heparin solution. No suggestion is made to form a matrix of polymerized aminosilane for receiving a thromboresistant material such as a heparinous material, and no suggestion is made concerning reacting a thromboresistant molecule to the amino groups on the aminosilane to provide a non-reversible reaction.

Many other approaches have been taken in the past when responding to the problem of imparting thromboresistant properties to artificial implants, prostheses and other devices for contacting body fluids and the like. They typically are deficient, especially from the point of view of providing an efficient means for securing or adhering the antithrombogenic agent to the fluid-contacting surface.

It has been found that, by proceeding in accordance with the present invention, it is possible to efficiently produce thromboresistant coatings onto surfaces of medical devices through an approach that provides attachment of an antithrombogenic agent in a manner that can be readily controlled so as to achieve a thromboresistant coating that can be reproduced in a consistent manner. In summary, the invention coats the surface of the device that is to be rendered thromboresistant with an aminosilane-containing composition which is then subjected to curing conditions in order to thereby form an aminosilane polymeric matrix. Typically this matrix formation is carried out under controlled time, temperature and humidity conditions until a matrix having the desired physical structure and chemical moieties is provided. Thereafter, an antithrombogenic agent is chemically secured to the aminosilane polymer matrix in order to form the thromboresistant coating onto the fluid-contacting surface of the medical device.

It is a general object of the present invention to provide an improved thromboresistant coating, a medical device having the thromboresistant coating, and a method for preparing same.

Another object of the present invention is to provide an improved thromboresistant coating, article and method which utilize a three-dimensional matrix containing aminosilanes for securely attaching antithrombogenic agents to a surface intended for contacting blood and the like.

Another object of the present invention is to provide an improved thromboresistant coating, article and method which allow for attachment of antithrombogenic agents to surfaces of prostheses and other medical devices in a controlled and efficient manner.

Another object of this invention is to provide an improved thromboresistant coating, device and method which can exhibit a desired hydrophilicity.

Another object of the present invention is to provide an improved thromboresistant coating, device and method which can be adjusted in order to achieve a desired degree of uptake and elution of the antithrombogenic agent.

Another object of this invention is to provide an improved thromboresistant coating, device and method which can provide a coating having improved elastomeric properties.

Another object of the present invention is to provide an improved thromboresistant coating, device and method which can provide an increased extent of drug loading onto and/or into the coating.

Another object of the present invention is to provide a thromboresistant coating, device and method which provide a three-dimensional matrix that is cured as a film substantially thicker than that typically found when silane priming agents or coupling agents are used.

Another object of the present invention is to provide a thromboresistant coating, device and method which utilize a coupling component applied without a solvent or only minimal amounts of a solvent.

These and other objects, features and advantages of this invention will be clearly understood through a consideration of the following detailed description.

DESCRIPTION OF THE PARTICULAR EMBODIMENTS

According to the present invention, a thromboresistant coating is applied to the surface of a medical device, which surface is intended for contact with blood and/or other body fluids and/or fluids for use within the body. Illustrative of medical devices, prostheses and other structures that can be treated according to the present invention include catheters, vascular grafts, cardiac pacemaker leads, heart diaphragms, heart valves, sutures, needles, angioplasty devices, glass beakers, dialysis membranes, filters, sensors and the like. In general, devices that have especially smooth surfaces may be more difficult to treat in accordance with this invention.

For example, it may be useful for devices such as catheters and the like to be provided with an outside surface that is roughened or textured A device such as a polymer vascular graft and the like often provides surface undulations or irregularities that eliminate any possible need for adding texture to the surface of the polymer itself.

Devices of this type can exhibit surfaces of any of a variety of materials, including polytetrafluoroethylenes, polyamides, polyesters, polyurethanes, polysiloxanes, polyolefins, metals and the like. Typically, best results are achieved if the substrate surface is one in which the matrix formed according to the present invention is reactive with the surface of the substrate in order to thereby provide especially advantageous adhesion. Accordingly, preferred substrate materials are those which contain active hydrogen moieties Exemplary substrate materials in this regard include acetoxy derived silicones, polyurethanes, nylons and the like, each of which contains active hydrogens which react directly with aminosilanes of the matrix according to the present invention.

In the event that it is desired to apply the thromboresistant coating to surfaces that are more inert than these types of preferred substrate materials, adhesion can be greatly facilitated by chemically treating such inert surfaces in order to provide hydroxyl groups on or near the surface thereof. Exemplary chemical surface treatments in this regard include such known procedures as chemical etching, surfactant adsorption, coextrusion, plasma discharge, surface oxidation or reduction, radiation activation and oxidation, and surface grafting with materials such as polyvinyl alcohol, poly(2-hydroxyethyl methacrylate) and the like. Bulk modifications of the substrate surface can also be accomplished in order to provide active hydrogens. Examples of conventional modifications of this type include blending with polymers having active hydrogens, partial degradation of polymers, end group modification, monomer functionalization, oxidation, reduction, copolymerization, and the like.

Once the desired device and substrate surface are selected or treated or modified as necessary, a three-dimensional, highly crosslinked matrix containing aminosilanes is formed on this medical device surface. The aminosilane is cured, crosslinked or polymerized in place on the surface to be rendered thromboresistant. This is carried out in a manner such that a three-dimensional matrix is formed. The matrix can be either an aminosilane homopolymer or a copolymer, including a graft copolymer, of an aminosilane with another silane that is not an aminosilane.

Aminosilanes thus used in accordance with this invention are ones having the following general formula: $H_2N\text{-}R'\text{-}Si(OR)_3$ or $H_2N\text{-}R'\text{-}SiX_3$. In this formula, OR is a typical silane leaving group, such as methoxy, ethoxy, acetoxy and the like, as well as mixtures thereof, or the OR group can be a hydroxyl group and X can be a halogen such as chlorine and the like. The R' group, which can be characterized as a spacer arm, is typically an alkyl group, an aromatic group, an ether, an ester or an imine-containing group. Exemplary R' groups are the low to moderate length alkyl chains such as methyl, ethyl, propyl, butyl and up to as high as about C-9 or more. R' aromatic groups include phenyl groups, and imine groups include aminopropyl groups and the like. Representative aminosilanes include 3-aminopropyltrimethoxysilane, 3-aminopropyltriethoxysilane, 2-aminoundecyltrimethoxysilane, aminophenyltrimethoxysilane, N-(2-aminoethyl-3-aminopropyl)trimethoxysilane, and trimethoxysilylpropyldiethylenetriamine. Aminosilanes of this type can be used alone in order to form a homopolymer matrix.

These aminosilanes are trifunctional and provide a highly crosslinked matrix. Because the matrix is hydrophilic, they are especially suitable when an initial high burst of antithrombogenic agent is required for the particular medical device being rendered thromboresistant. The hydrophilicity can be reduced, when desired, by combining the hydrophilic aminosilane with a less hydrophilic silane that is not an aminosilane Accordingly, in some instances, it may be desired to provide a matrix that is a copolymer of one of these aminosilanes with another silane molecule that is not an aminosilane and that is less hydrophilic than an aminosilane in order to thereby adjust the hydrophilicity of the matrix. One such silane component that is not an aminosilane is illustrated by the formula:

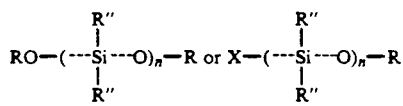

wherein this formula represents a block having a desired chain length wherein n is generally between one and about 300,000, wherein the RO or X group is of the type described herein as an OR or X group, wherein the R (together with the terminal O of the block) is a group of the type described herein as an OR or X group, and wherein the R'' groups are typically aliphatic groups of C-1 to about C-9, aromatic groups such as phenyl groups or substituted phenyls, or combinations or mixtures thereof Examples of typical polymer blocks are acetoxy terminated polydimethyl siloxanes, acetoxy terminated polydiphenylsiloxanes, and the like.

Another suitable silane that is less hydrophilic than an aminosilane according to, this invention has the formula: $R''_x\text{-}Si(OR)_y$ or $R''_x\text{-}SiX_y$ wherein R'', X, and OR are as defined herein, and wherein x is an integer between zero and three and y is an integer between one and four such that the sum of x and y equals four. Exemplary silane components according to this formula include dimethyldimethoxysilane, methyltrimethoxysilane, propyltriacetoxysilane, and the like.

When these other silane components which are not aminosilanes are copolymerized with the aminosilanes, it is preferred that the silane component be generally hydrophobic when compared with the aminosilane with which it is copolymerized and/or graft polymerized. In a typical graft polymerization approach, the silane that is not an aminosilane preferably is first applied and substantially cured, and the aminosilane is subsequently graft polymerized thereto by a mechanism that is believed to include condensation between SiOH groups of the substantially cured silane and the silane of the aminosilane grafted onto the cured silane. By such a copolymerization approach, it is possible to control the hydrophilicity of and the resulting degree of drug elution and immobilization provided by the matrix. It is also possible to thereby impart improved elastomeric properties to the matrix and to the thromboresistant coating. Such also renders possible an increase in the quantity and type of drugs that can be loaded into and/or onto the thromboresistant coating matrix.

The aminosilane homopolymer or copolymer forms a three-dimensional matrix, which is a polymeric matrix that is different from that provided by a typical silane priming agent or coupling agent. Such typical silane priming agents or coupling agents are applied in low concentration and with substantial quantities of a solvent therefor so as to provide what may be characterized as a silane monolayer that is formed from solution The three-dimensional matrix according to the present invention is one in which the aminosilane component is applied without a solvent or with relatively low quantities of a diluent solvent that can be useful to adjust the viscosity of the aminosilane component. In other words, the aminosilane component according to the present invention is applied neat, or it is applied with only minimal dilution in order to adjust the viscosity so as to improve the handling properties of some aminosilane components.

Lowering the viscosity of the aminosilane component polymer system facilitates wetting of the substrate surface with the silanating system. The diluent which can be included for this purpose can also provide the typically advantageous function of slightly swelling the substrate surface. A typical diluent useful in this regard can include appropriate low molecular weight alcohols, such as methanol, ethanol, isopropyl alcohol and the like, as well as halogenated solvents such as 1,1,1-trichloroethane, chloroform, methylene chloride, tetrachloroethylene, fluorosolvents, and the like. The diluent can also include hydrolyzing solvents such as water or mixtures of water and other diluents such as those specified above.

When the diluent is used, the aminosilane component will comprise at least about 2 percent by weight or more of the viscosity-adjusted composition. In other words, the composition that is used to form the three-dimensional matrix according to the present invention includes between about 2 weight percent and 100 weight percent of the aminosilane component that is used in forming the homopolymer or copolymer three dimensional matrix. Generally speaking, it is preferred that the aminosilane component be combined for copolymerization or graft copolymerization when aminosilane concentrations at the lower portion of this range are utilized. For example, it can be preferable to include at least about 10 weight percent of aminosilane when a homopolymer matrix is formed.

After such a composition is applied, it is cured as a thick film having a thickness of between about 0.01 and about 20 microns, with the thickness being substantially greater than that of silane priming agents or coupling agents that are applied in dilute solution to form monolayers, dilayers or trilayers, each having a thickness of less than ten Angstrom units. The thus applied amino silane component is cured as a thick film in a humid oven, preferably before any rinsing in order to minimize the chance that aminosilane monomer would dissolve out and leave only a very thin primed layer.

Typically, the aminosilane component will be dip coated onto the substrate to be rendered thromboresistant, although any other application means can be provided which allows for the easy application of a thick layer of the aminosilane component. Once thus applied, the surface being rendered thromboresistant is subjected to drying conditions under controlled time, temperature and humidity conditions. Generally speaking, drying of the aminosilane component so as to form the three-dimensional matrix can be carried out for approximately twenty-four hours at room temperature, with it being possible to achieve the desired result in about ten minutes at a drying temperature of about 110° C. Variations between these can also be practiced. A typically preferred time and temperature combination is to carry out the drying for about two hours at approximately 80° C.

With respect to the humidity conditions in effect during the drying or three-dimensional matrix formation procedure, it is preferred that the humidity be controlled in order to thereby enhance the formation of the three-dimensional matrix. It is preferred to control the humidity conditions such that a higher relative humidity environment is provided at the early stages of the curing or drying operation, with a decrease in the relative humidity near the end of the curing procedure. For example, at the beginning of the curing procedure, a 50 percent to 70 percent relative humidity environment will enable hydrolysis of the aminosilane component in the earlier stages of the curing procedure, while the humidity can be decreased to a relative humidity of 20 percent or below in order to thereby facilitate evaporation of any residual water or moisture toward the end of the curing step in order to thereby complete the formation of a three-dimensional matrix.

After this silanation reaction during which the aminosilane homopolymer or copolymer is formed has been completed, the thus formed three-dimensional silane matrix is able to be rinsed repeatedly in water without substantially modifying the three-dimensional matrix which is provided. Such rinsing of the matrix is preferably carried out repeatedly in order to remove any unreacted or unbound silane or polymer residue within the matrix.

Whether the aminosilane component or polymer system is one that includes only the aminosilane or the aminosilane combined with a comonomer silane, graft comonomer silane and/or a diluent, the aminosilane moiety is reacted to itself and to the substrate being rendered thromboresistant. When a comonomer component is also present, copolymerization also takes place. These reactions typically are carried out in the presence of heat and moisture in order to provide a three-dimensional graft polymer matrix which is believed to be covalently bound on the surface of the substrate. After rinsing to remove unreacted monomer, loose polymer and other residue, the cured silane matrix and (as necessary) the substrate surface are immersed in a solution containing the antithrombogenic agent. Conventional amine coupling techniques are used to have the antithrombogenic agent be bound to the amine group on the aminosilane three-dimensional matrix.

Antithrombogenic agents or materials are those components which inhibit thrombus formation on surfaces having the antithrombogenic material. Thrombus formation is reduced by performing functions such as reducing platelet aggregation, dissolving fibrin, enhancing passivating protein deposition and/or inhibiting one or more steps within the coagulation cascade. Illustrative antithrombogenic agents or materials include various heparinous materials. Specific examples of these antithrombogenic agents include heparin, prostaglandin, hirudin, urokinase, streptokinase, a sulfated polysaccharide, albumin, fibronectin, laminin, a tissue plasminogen activator, collagen, gelatin, hyalraunic acid, combinations thereof, and the like. The antithrombogenic agent or material may be used in amounts suitable for the particular agent or material employed, the particular matrix to which it is secured, and the antithrombogenic result that is desired. Typically, these antithrombogenic agents will comprise not more than about 5 percent by weight of the thromboresistant coating, typically between about 0.01 weight percent and about 5 weight percent.

At times, it is preferred that the antithrombogenic material include a biological or synthetic extender which may be bound to a thrombogenic agent, which bound combination can be considered to be an antithrombogenic agent or material. Often the extenders themselves have antithrombogenic properties. Illustrative extenders include albumin, gelatin, collagen, fibronectin, hyalraunic acid, laminin, dextrose, polysaccharides, protamine, polyethyleneimine, polyvinyl pyrrolidone, amine-terminated polyethyleneglycol, combinations thereof and the like. Typically, such extenders are multi-functional and usually contain amine groups, and the extenders can be bonded both to the aminosilane three-dimensional matrix as well as to the antithrombogenic agent or drug itself. Typical bonding reactions of these amine-containing extenders include mechanisms such as formaldehyde crosslinking gluteraldehyde crosslinking, diisocyanate coupling, diacid chloride coupling, diglycidil coupling, ionic bonding and the like.

With regard to the mechanism by which the antithrombogenic material (including its extender, when present) is bound to the aminosilane three-dimensional matrix, a number of different binding schemes are available The antithrombogenic agent can be adsorbed, ionically bound or covalently bound into the extender or matrix. These approaches are generally known.

When adsorption is utilized, it takes advantage of the positively charged group on the amine of the matrix. As an example, heparin is dissolved in water at a 0.2 percent concentration and adjusted to a pH of between 3 and 5. A substrate containing the cured and cleansed aminosilane three-dimensional matrix according to the present invention is immersed into this heparin solution for 24 hours at 50° C., after which the device is removed and rinsed. It is believed that with this approach, heparin is ionically bound to the aminosilane matrix. Positive staining with toluidine blue confirms heparin uptake. The heparin will eventually elute out as desired and over a time period that can be varied according to the ratio of aminosilane to hydrophobic comonomers or blocks present in the matrix.

Covalent binding of heparin or other thrombogenic agent to artificial surfaces is generally illustrated in Larm, Larsson and Olsson, "A New Non-Thrombogenic Surface Prepared by Selective Covalent Binding of Heparin Via a Modified Reducing Terminal Residue", J. Biomat. Med. Dev., Art. Org., 11 (2 & 3), pp. 161-173 (1983), the disclosure thereof being incorporated by reference hereinto. In this arrangement, heparin is partially degraded such that aldehyde groups are formed on the molecule. The aldehyde groups are then reacted with the amine group on the aminosilane or extender.

It will be appreciated that other techniques for activating antithrombogenic agents may be utilized. Included are techniques that add activating components such as N-ethyl-5-phenylisoxazolium-3'-sulfonate, 1-ethyl-3-(3-dimethyl-aminopropyl)carbodiimide hydrochloride, and 1-cyclohexyl-3-(2-morpholinoethyl)carbodiimide.

EXAMPLE 1

A polyurethane catheter was dipped into 100 percent or neat N-(2-aminoethyl-3-aminopropyl)trimethoxysilane, which is available from Petrarch Systems under the trade designation A0700, to provide a thick coating of the aminosilane. The aminosilane coating was then polymerized by transferring the catheter to an oven for drying or curing. For the first two hours of drying, the oven was set at 50° C. and at a relative humidity of 60 percent. Thereafter, vacuum drying was carried out for two additional hours at 100° C. in order to complete formation of the polymeric matrix. The catheter was then rinsed repeatedly in distilled water for thirty minutes, and the water was discarded twice during this rinsing operation.

Heparin was oxidized according to the method of Larm, Larsson and Olsson. More particularly, one gram of heparin was dissolved in 300 ml of distilled water at 0° C. Then, 10 mg of sodium nitrate was added, and the pH value was adjusted to 2.7 by the addition of 1 M hydrochloric acid. Stirring at 0° C. was carried out for two hours. The pH value was then adjusted to 7.0 with aqueous sodium hydroxide, and the reaction mixture was thoroughly dialyzed against ultrapure water (3 times with 1000 ml), and then diluted to 500 ml with pure water. This oxidized heparin solution was stored in a refrigerator at 4° C. until use. Just prior to use, 5 mg of cyanoborohydrate and 0.15 M of sodium chloride were added to the heparin solution, and the pH was adjusted 3.5.

The catheter containing the aminosilane polymer matrix was then immersed into this heparin solution for two hours at 50° C. Thereafter, it was rinsed repeatedly in distilled water. Toluidine dye uptake stained positive for heparin, and when compared with a non-treated control catheter, the thromboresistant coated catheter according to this invention showed significant improvement with regard to thrombus buildup on the surface of the catheter.

EXAMPLE 2

A polyurethane catheter was dipped into a component containing 50 percent by weight of N-(2-aminoethyl-3-aminopropyl)trimethoxysilane and 50 percent isopropanol diluent to provide a thick coating of unreacted aminosilane component. Thereafter, the catheter was dried in an oven at 60 percent relative humidity and 50° C. for four hours, after which the catheter was rinsed repeatedly in distilled water for thirty minutes, discarding the water twice during this procedure. The catheter containing the thus formed three-dimensional amino silane matrix was then reacted with a 0.2 percent heparin solution containing 1-ethyl-3-(3-dimethylaminopropyl)carbodiimide hydrochloride according to the procedure specified in Solomon et al U.S. Pat. No. 4,521,564, the disclosure thereof being incorporated by reference hereinto. Positive staining was achieved with toluidine blue. When compared with a non-treated catheter, the catheter containing the thromboresistant coating according to this Example showed significant improvement with regard to thrombus buildup on the surface of the catheter.

EXAMPLE 3

Acetoxy-terminated polydimethyl siloxane (5 percent weight/volume) was dissolved in 1,1,1-trichloroethane, and a catheter made of hydroxyl-terminated polyurethane was dipped thereinto and cured at room temperature at 60 percent relative humidity for 24 hours. The thus coated catheter was then dipped into an aminosilane composition of 2 weight percent of the aminosilane of Example 1 in water, and this composition was then dried at 100° C. for two hours and under vacuum for an additional two hours in order to form a matrix that is a graft polymerized copolymer of the aminosilane onto the polymerized siloxane.

Oxidized heparin was reacted to the three-dimensional aminosilane matrix, such being generally in accordance with the procedure specified in Example 1. Samples stained positive with toluidine blue, and when compared with a non-treated control, showed significant improvement in reduced thrombus buildup on the surface of the catheter.

EXAMPLE 4

A polyethylene catheter was exposed to an oxidizing solution containing potassium dichromate. This oxidized surface was then exposed to the silane comonomer system of Example 3. In this example, non-oxidized heparin and oxidized heparin were absorbed and bound into the aminosilane/polydimethylsiloxane graft copolymer matrix. The three-dimensional matrix was well adhered. It eluted heparin, and it also contained covalently bound heparin on the surface. When compared with a non-treated control, this catheter showed significant improvement with regard to thrombus buildup on its surface.

EXAMPLE 5

A porous vascular graft constructed of hydroxy-terminated polyurethane was coated with the comonomer system of Example 3, followed by curing into the three-dimensional graft copolymer matrix and washing. The graft was then immersed in a mixture of 1 percent gelatin and 0.2 percent protamine for 10 minutes under vacuum. The components of the gelatin/protamine/aminosilane system were then crosslinked together using 0.25 percent gluteraldehyde solution during a one hour time period. Heparin was then coupled to protamine by immersing the vascular graft into a 0.2 percent solution of heparin for four hours at 24° C. When compared with a non-treated control vascular graft, the graft of this example showed significant improvement with regard to thrombus buildup.

EXAMPLE 6

A catheter was extruded from a polyurethane that was made with an isocyanate-to-hydroxyl ratio that was less than 1. This hydroxyl-rich catheter sheath was dipped in an aminosilane composition containing 75 weight percent of the aminosilane of Example 1 and 25 weight percent isopropanol diluent. The thick coating was then formed into the three-dimensional matrix by drying same for one hour at 80° C. and 75 percent relative humidity, followed by oven drying for one hour at 80° C. and 10 percent relative humidity. The resulting material was rinsed well in water and dried. The tip of the catheter was then thermoformed at 100° C. into a pigtail shape. The catheter was then immersed in 0.2 percent oxidized heparin for four hours, followed by rinsing, drying and packaging. This Example showed significant improvement, when compared with a non-treated control catheter, in reducing the extent of thrombus buildup on the surface of the catheter.

It will be understood that the embodiments of the present invention which have been described are illustrative of some of the applications of the principles of the present invention. Numerous modifications may be made by those skilled in the art without departing from the true spirit and scope of the invention.

I claim:

1. A thromboresistant coating for a medical device having a body fluid-contacting surface for contacting blood, other body fluids and the like, the thromboresistant coating comprising:

a three-dimensional copolymeric matrix secured to the body fluid-contacting surface of the medical device, said copolymeric matrix being a copolymer including an aminosilane of the formula: $H_2N-R'-Si(OR)_3$ or $H_2N-R'-SiX_3$, wherein R' is a spacer group selected from the group consisting of alkyl groups, aromatic groups and imine-containing groups, wherein OR is an alkoxy group or an hydroxy group and wherein X is a halogen, wherein said copolymeric matrix is a copolymer or graft copolymer of said aminosilane and of a silane other than said aminosilane, and wherein said copolymer matrix was polymerized from a composition that contains substantially only the aminosilane and the silane other than said aminosilane; and an antithrombogenic material secured to said aminosilane copolymeric matrix.

2. The thromboresistant coating according to claim 1, wherein said other silane has the formula:

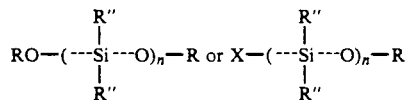

wherein RO is an alkoxy group or an hydroxy group, wherein X is a halogen, wherein R'' is a group selected from the group consisting of alkyl groups, aromatic groups and combinations thereof, wherein n designates the number of silane blocks and is between 1 and about 300,000, and wherein R, together with the terminal O of the terminal silane block is an alkoxy group, an hydroxy group or a halogen.

3. The thromboresistant coating according to claim 1, wherein said other silane is of the formula: $R''_x-Si(OR)_y$ or $R''_x-SiX_y$ wherein OR is an alkoxy group or an hydroxy group, wherein X is a halogen, wherein R'' is a group that is an alkyl group, an aromatic group or combinations thereof, and wherein the sum of x and y is four.

4. The thromboresistant coating according to claim 1, wherein said other silane is an acetoxy terminated polysilane.

5. The thromboresistant coating according to claim 4, wherein said aminosilane is N-(2-aminoalkyl-3-aminoalkyl)trialkoxysilane.

6. The thromboresistant coating according to claim 5, wherein said antithrombogenic material includes an extender bound thereto and bound to said copolymeric matrix.

7. A medical device having a thromboresistant coating over a body fluid-contacting surface of the medical device for contacting blood, other body fluids and the like, wherein the thromboresistant coating comprises:

a three-dimensional copolymeric matrix secured to the body fluid-contacting surface of the medical device, said copolymeric matrix being a copolymer including an aminosilane of the formula: $H_2N-R'-Si(OR)_3$ or $H_2N-R'-SiX_3$, wherein R' is a spacer group selected from the group consisting of alkyl groups, aromatic groups and imine-containing groups, wherein OR is an alkoxy group or an hydroxy group and wherein X is a halogen,
wherein said copolymeric matrix is a copolymer or graft copolymer of said aminosilane and of a silane other than said aminosilane, and wherein said copolymer matrix was polymerized from a composition that contains substantially only the aminosilane and the silane other than said aminosilane; and an antithrombogenic material secured to said aminosilane polymeric matrix.

8. The medical device according to claim 7, wherein said copolymeric matrix is a graft copolymer of said aminosilane onto a polymer of the silane other than said aminosilane.

9. The medical device according to claim 8, wherein said antithrombogenic material includes an extender bound to said graft copolymer.

* * * * *